(12) United States Patent
Andresen et al.

(10) Patent No.: US 8,334,395 B2
(45) Date of Patent: Dec. 18, 2012

(54) HYDROCARBON/OXYGEN INDUSTRIAL GAS MIXER WITH COARSE WATER DROPLET ENVIRONMENT TO REDUCE IGNITION POTENTIAL

(75) Inventors: Harvey E. Andresen, Luling, LA (US); Christopher P. Christenson, Lake Jackson, TX (US); Charles W. Lipp, Lake Jackson, TX (US); John R. Mayer, The Woodlands, TX (US); Thomas J. Kling, Midland, MI (US); Victor R. Fey, West Bloomfield, MI (US); Laurence G. Britton, Charleston, WV (US); Michael J. Rangitsch, Saginaw, MI (US); Michael L. Hutchison, Poca, WV (US)

(73) Assignee: Dow Technology Investments LLC, Midland, MI (US)

( * ) Notice: Subject to any disclaimer, the term of this patent is extended or adjusted under 35 U.S.C. 154(b) by 364 days.

(21) Appl. No.: 12/678,276

(22) PCT Filed: Nov. 7, 2008

(86) PCT No.: PCT/US2008/012587
§ 371 (c)(1),
(2), (4) Date: Mar. 15, 2010

(87) PCT Pub. No.: WO2009/078898
PCT Pub. Date: Jun. 25, 2009

(65) Prior Publication Data
US 2010/0204496 A1    Aug. 12, 2010

Related U.S. Application Data

(60) Provisional application No. 61/007,658, filed on Dec. 14, 2007.

(51) Int. Cl.
*C07D 301/08* (2006.01)
*B01J 19/00* (2006.01)

(52) U.S. Cl. ................................ 549/523; 422/224
(58) Field of Classification Search .................. 549/523; 422/224
See application file for complete search history.

(56) References Cited

U.S. PATENT DOCUMENTS

| | | |
|---|---|---|
| 2,614,616 A | 10/1952 | Villoresi et al. |
| 2,981,747 A | 4/1961 | Lang et al. |
| 2,998,465 A | 8/1961 | Drummond et al. |
| 3,081,818 A | 3/1963 | Braconier et al. |
| 3,237,923 A | 3/1966 | Turner |
| 3,518,284 A | 6/1970 | Foster |
| 3,570,471 A | 3/1971 | Lazaridis |
| 3,702,619 A | 11/1972 | Son |
| 3,706,534 A | 12/1972 | Verheul et al. |
| 4,012,469 A | 3/1977 | Accortt |
| 4,256,604 A | 3/1981 | Aida et al. |
| 4,348,476 A | 9/1982 | Hou |
| 4,390,346 A | 6/1983 | Cramer et al. |
| 4,393,817 A | 7/1983 | Lindberg |
| 4,415,508 A | 11/1983 | Aida et al. |
| 4,564,298 A | 1/1986 | Gritters et al. |
| 4,573,803 A | 3/1986 | Gritters et al. |
| 4,926,620 A | 5/1990 | Donle |
| 5,037,619 A | 8/1991 | Alagy et al. |
| 5,178,654 A | 1/1993 | Cowley et al. |
| 5,250,267 A | 10/1993 | Johnson et al. |
| 5,336,791 A | 8/1994 | Jennings et al. |
| 6,231,648 B1 | 5/2001 | Marlowe |
| 6,657,079 B1 | 12/2003 | Tetsuji et al. |
| 6,713,036 B1 | 3/2004 | Vanden Bussche et al. |
| 6,840,256 B1 | 1/2005 | Ryan et al. |
| 6,953,495 B2 | 10/2005 | Schwab |
| 7,108,838 B2 | 9/2006 | McGee |
| 2003/0021182 A1 | 1/2003 | Illy et al. |
| 2003/0175183 A1 | 9/2003 | Guetlhuber |
| 2004/0062689 A1 | 4/2004 | Gauthier et al. |
| 2006/0036106 A1 | 2/2006 | Mazanec et al. |
| 2006/0231645 A1 | 10/2006 | Chan |

FOREIGN PATENT DOCUMENTS

| | | |
|---|---|---|
| DE | 102005020942 | 11/2006 |
| EP | 0006734 | 1/1980 |
| EP | 0026827 | 4/1981 |
| EP | 1705167 | 9/2006 |
| EP | 1726355 | 11/2006 |
| GB | 672446 | 5/1952 |
| GB | 705176 | 3/1954 |

(Continued)

OTHER PUBLICATIONS

PCT International Search Report, PCT International Application No. PCT/US2008/012587, mailed Feb. 10, 2009.

(Continued)

*Primary Examiner* — Bernard Dentz
(74) *Attorney, Agent, or Firm* — McDonnell Boehnen Hulbert & Berghoff LLP (57) ABSTRACT

A hydrocarbon-containing gas is mixed with an oxygen gas in a gas mixer in the presence of coarse water droplet environment, e.g., a 'rainy' or 'driving rainstorm' environment in which the water droplets generally have a size greater than 200 microns SMD. The water droplets surround and contact entrained particles in either the oxygen gas stream or the hydrocarbon-containing gas stream. The water acts to suppress, prevent and quench ignition of the hydrocarbon gas in the mixer which would otherwise be caused by energetic collisions between such particles and structures within the gas mixer. In one configuration the gas mixer includes water pipes having coarse water droplet-producing nozzles at the peripheral end thereof concentrically located within oxygen supply pipes. Additionally, nozzles introduce coarse water droplets into a pipe carrying the hydrocarbon gas and forming a mixing chamber for the hydrocarbon and oxygen gases.

20 Claims, 4 Drawing Sheets

FOREIGN PATENT DOCUMENTS

| | | |
|---|---|---|
| GB | 1262436 | 2/1972 |
| GB | 1368922 | 10/1974 |
| GB | 2009174 | 6/1979 |
| GB | 2357318 | 6/2001 |
| JP | 55061927 A | 5/1985 |
| JP | 55064579 A | 5/1985 |
| TW | 590803 | 6/2004 |
| WO | WO01/85873 | 11/2001 |
| WO | WO2007/045457 | 4/2007 |
| WO | WO2009/078897 | 6/2009 |
| WO | WO2009/078899 | 6/2009 |
| WO | WO2009/078900 | 6/2009 |
| WO | WO2009/102311 | 8/2009 |

OTHER PUBLICATIONS

PCT International Search Report, PCT International Application No. PCT/US2008/012716, mailed Oct. 5, 2009.
PCT International Search Report, PCT International Application No. PCT/US2008/012715, mailed Feb. 3, 2009.
PCT International Search Report, PCT International Application No. PCT/US2008/012714, mailed Mar. 10, 2009.
PCT International Search Report, PCT International Application No. PCT/US2008/012586, mailed Feb. 11, 2009.
PCT Written Opinion, PCT International Application No. PCT/US2008/012587, mailed Feb. 10, 2009.
PCT Written Opinion, PCT International Application No. PCT/US2008/012716, mailed Oct. 5, 2009.
PCT Written Opinion, PCT International Application No. PCT/US2008/012715, mailed Nov. 19, 2009.
PCT Written Opinion, PCT International Application No. PCT/US2008/012714, mailed Mar. 10, 2009.
PCT Written Opinion, PCT International Application No. PCT/US2008/012586, mailed Feb. 11, 2009.
PCT International Preliminary Report on Patentability, PCT International Application No. PCT/US2008/012587, mailed Feb. 22, 2010.
PCT International Preliminary Report on Patentability, PCT International Application No. PCT/US2008/012586, mailed Feb. 22, 2010.
U.S. Appl. No. 12/678,257, Low Shear Gas Mixer, filed Mar. 15, 2010.
U.S. Appl. No. 12/678,263, Wet Scrubbing for Removing Particulate Solids From Oxygen Supply Line, filed Mar. 15, 2010.
U.S. Appl. No. 12/678,270, Oxygen/Hydrocarbon Rapid (High Shear) Gas Mixer, Particularly for the Production of Ethylene Oxide, filed Mar. 15, 2010.
U.S. Appl. No. 12/678,274, Hydrocarbon/Oxygen Industrial Gas Mixer With Water Mist, filed Mar. 15, 2010.
PCT International Preliminary Report on Patentability, PCT International Application No. PCT/US2008/012716, mailed Jun. 24, 2010.
PCT International Preliminary Report on Patentability, PCT International Application No. PCT/US2008/012714, mailed Jun. 24, 2010.
PCT International Preliminary Report on Patentability, PCT International Application No. PCT/US2008/012715, mailed Mar. 29, 2010.
Burkholz, Armin, "Droplet Separation", 1989, pp. 180-182, VCH Publishers, New York, NY.
Mawhinney et al., Halon Options Technical Working Conference, Protecting Against Vapor Explosions With Water Mist, 215-226, May 2-4, 2000.
U.S. Appl. No. 12/678,270, Office Action mailed Jul. 12, 2012.
U.S. Appl. No. 12/678,274, Office Action mailed Jul. 16, 2012.
U.S. Appl. No. 12/678,257, Response to Office Action mailed Mar. 16, 2012, filed Jun. 15, 2012.
U.S. Appl. No. 12/678,257, Office Action mailed Mar. 16, 2012.

HYDROCARBON/OXYGEN INDUSTRIAL GAS MIXER WITH COARSE WATER DROPLET ENVIRONMENT TO REDUCE IGNITION POTENTIAL

CROSS-REFERENCE TO RELATED APPLICATIONS

This application is a U.S. National Phase of International Application No. PCT/US2008/012587, filed Nov. 7, 2008, which claims priority to U.S. Provisional Application No. 61/007,658, filed Dec. 14, 2007, all of which are herein incorporated by reference in their entirety.

BACKGROUND

This invention relates generally to gas mixers used in systems for gas-phase partial oxidation of hydrocarbon-containing gases. An example of where this invention has utility is systems for industrial production of ethylene oxide.

The chemical compound ethylene oxide (chemical formula $C_2H_4O$) is an important industrial chemical used as an intermediate in the production of ethylene glycol (the main component of automotive antifreeze) and other chemicals. Ethylene oxide is also used as a sterilant for foods and medical supplies. It is a colorless flammable gas at room temperature, and can be cooled and stored as a liquid.

Ethylene oxide first achieved industrial importance during World War I as a precursor to both ethylene glycol and the chemical weapon mustard gas. In 1931, Theodore Lefort, a French chemist, discovered a means to prepare ethylene oxide directly from ethylene and oxygen, using silver as a catalyst. Since 1940, almost all ethylene oxide produced industrially has been made using this method.

In current industrial processes, ethylene oxide is produced when ethylene ($CH_2$=$CFl_2$) and oxygen ($O_2$) react on a silver catalyst at 200-300° C. showing large Ag nanoparticles supported on Alumina. Typically, chemical modifiers such as chlorine are also included. Pressures used are in the region of 1-2 MPa. The chemical equation for this reaction is:

$$CH_2=CH_2+\tfrac{1}{2}O_2 \rightarrow C_2H_4O$$

In ethylene oxide production systems, a gas mixer is used to mix the hydrocarbon-containing gas stream and the oxygen gas stream just upstream of the reaction chamber where the silver catalyst is present. The gas mixer is typically constructed in the form of a vessel or pipe. The vessel includes an inlet manifold for each of the two gases. The vessel is sometimes constructed with a main outer pipe containing the hydrocarbon gas stream and internal concentric tubes or "fingers" which contain the oxygen stream. Mixing occurs at the point where the internal tubes end, where the oxygen gas flowing out of the fingers meets the main stream of hydrocarbon gas flowing in the outer tube. This basic design is described in U.S. Pat. No. 3,706,534.

The art has long recognized that there is a risk of ignition of a hydrocarbon-containing gas stream (e.g., a stream of gas containing for example ethylene mixed with other hydrocarbon gases) at the point where it is combined with an oxygen gas in a gas mixer. Ignition can occur when a particle (e.g. a piece of sand, rust or pipe scale) entrained in the hydrocarbon-containing gas stream or the oxygen gas stream strikes a metallic surface in the mixer, e.g., the wall of the mixer, thereby producing a spark. If the spark occurs in the hydrocarbon-containing gas stream in the highly flammable zone e.g., at, or close to, the point of mixing of the two gas streams, ignition can occur. The ignition may damage the gas mixer and also requires an interrupt of production to suppress the ignition and allow the gas mixer to cool before recommencing production. The flammable region is confined to the mixing zone of the two gases. The hydrocarbon-containing gas as well as the reactor feed blend are below the lower $O_2$ flammability limit—i.e., too rich to burn.

The art has devised a variety of gas mixer designs. Some of the designs are specifically directed to reducing the risk of ignition of hydrocarbon-oxygen gas streams. The known prior art includes the following patent documents, in addition to the above-cited '534 patent: U.S. Pat. No. 4,573,803; U.S. Pat. No. 3,702,619; U.S. Pat. No. 4,256,604; U.S. Pat. No. 4,415,508; U.S. Pat. No. 6,657,079; U.S. 2003/0021182; U.S. Pat. No. 3,518,284; U.S. U.S. Pat. No. 4,390,346; U.S. Pat. No. 3,237,923; U.S. Pat. No. 3,081,818; U.S. Pat. No. 2,614,616 and U.S. Pat. No. 6,840,256.

Other prior art of interest include British patents GB 705,176 and 2,357,318; U.S. Pat. No. 5,336,791; and U.S. Pat. No. 4,393,817.

SUMMARY

In a first aspect of this disclosure, industrial production systems for gas-phase partial oxidation of a hydrocarbon-containing gas are disclosed which use a method for mixing the hydrocarbon-containing gas with an oxygen containing gas. The method includes providing a gas mixer having a mixing chamber for mixing the oxygen containing gas with the hydrocarbon-containing gas, producing a coarse water droplet environment in the mixing chamber of the gas mixer, and mixing the oxygen containing gas and the hydrocarbon-containing gas in the presence of the coarse water droplet environment. The invention can be applied to hydrocarbon-air mixers and hydrocarbon-enriched air mixers. Hence, the term "oxygen containing gas" is intended to encompass a stream of a gas containing oxygen generally, such as for example a stream of pure or substantially pure oxygen gas, a stream of air, or a stream of air which is enriched with oxygen gas. Similarly, the hydrocarbon-containing gas may include a pure hydrocarbon gas, or a hydrocarbon gas mixed with other gases, e.g., recycle gas in an EO production scenario.

In another aspect, an improvement to a gas mixer for an industrial production system for gas-phase partial oxidation of a hydrocarbon-containing gas is provided. The improvement is providing a means for producing a coarse water droplet environment in the gas mixer wherein the oxygen containing gas and the hydrocarbon-containing gas are mixed in a mixing chamber of the gas mixer in the presence of the coarse water droplet environment. Several examples of the means for producing the coarse water droplet environment are described, including atomizers (spray nozzles) which inject coarse water droplets into the mixing chamber, wherein the hydrocarbon gas stream flows through the coarse water droplet environment prior to meeting the oxygen gas stream. The design may also feature water pipes concentrically located within oxygen pipes carrying the supply of the oxygen gas to the mixing chamber and having nozzles at the end thereof which produce coarse water droplets wetting the oxygen gas stream prior to mixing with the hydrocarbon-containing gas stream.

DETAILED DESCRIPTION

In industrial production systems for gas-phase partial oxidation of a hydrocarbon-containing gas, such as production of ethylene oxide, the mixing of hydrocarbon and oxygen gases in a safe, reliable manner is a continuing problem, particularly when the gases to be mixed go through a flammable zone in the mixing process. The features of this disclosure provide improvements to a gas mixer and method of mixing gases which minimizes the probability of ignition. The mixing of the two gases is performed in a coarse water droplet environment. The coarse water droplet environment can be conceptualized as a rainstorm-like environment in the gas mixer. In a high pressure, high capacity application in which substantial amounts of water are needed, a substantial volume of water droplets are introduced into the gas mixer at high velocity, in effect creating a driving rainstorm environment at the point where the two gases are mixed.

Several different embodiments of a gas mixer featuring apparatus for producing the coarse water droplet environment will be described in some detail below. Applications include ethylene oxide production in a gas mixer featuring a low shear co-axial gas mixing. However, the invention can be practiced in a high shear gas mixer, such as described in WO2009/078899, entitled Oxygen/Hydrocarbon Rapid (High Shear) Gas Mixer, Particularly For The Production Of Ethylene Oxide, the entire content of which is incorporated by reference herein.

The purpose of the coarse water droplet environment is to reduce the probability of ignition of the flammable gas envelope where the two gases initially mix, or to quench an ignition should one initiate, by introducing a sufficient quantity of coarse water drops (Sauter Mean Diameter (SMD) greater than 200 microns) into the gas streams at the point of the high flammability gas envelope so as to provide enhanced mixing, wetting of the surface of any entrained particles in either the hydrocarbon stream or the oxygen stream, and a heat sink to transfer any heat generated from particle impact or particle fracture while the particle is still present in the flammable region in the mixer. In general, the gas mixer features atomizers (coarse water droplet producing nozzles) which are designed to produce water drops having a size >200 microns SMD. The term Sauter Mean Diameter (SMD) is used here to mean the diameter of a drop having the same volume/surface area ratio as the entire spray of the drops.

Materials of construction of the gas mixer and the water droplet generating devices may be stainless steel, Monel, Inconel, or other corrosion and ignition resistant metal. Such metals may also be used in the highest velocity zones and the gas-distributing pipes.

One application of the invention is direct oxidation ethylene oxide process mixers, which mix oxygen at intermediate pressure (~20 bar) with recycled hydrocarbon-containing gas containing ethylene and other gases. Oxygen pressures are approximately ~26 bar. The invention can similarly be used for other partial oxidation processes using pure oxygen or enriched air.

The features of this disclosure redefines the oxygen/hydrocarbon mixing process to reduce the potential for ignition in the flammable gas envelope that exists for some distance downstream of the point of injection of oxygen into the hydrocarbon-rich stream prior to complete mixing of the oxygen-hydrocarbon stream. The invention accomplishes this by mixing the gases in the presence of a coarse water droplet environment, to provide a heat sink to dissipate the impact energy of entrained particles in either the hydrocarbon or oxygen gas streams and to quench an ignition should one occur. The invention is particularly useful for mixing oxygen into the recycle gas containing ethylene in an ethylene oxide process.

The features of this disclosure provide a number of advantages and satisfy a long-felt need in the art. In particular, it allows for the injection of oxygen into a hydrocarbon-rich gas stream while minimizing the probability of igniting the gas. The advantage is particularly significant for a range of application in which gas mixing occurs at elevated pressures (e.g. 20 bar), which are commonly found in partial oxidation processes such as ethylene oxide production.

Example 1

Figure 1:
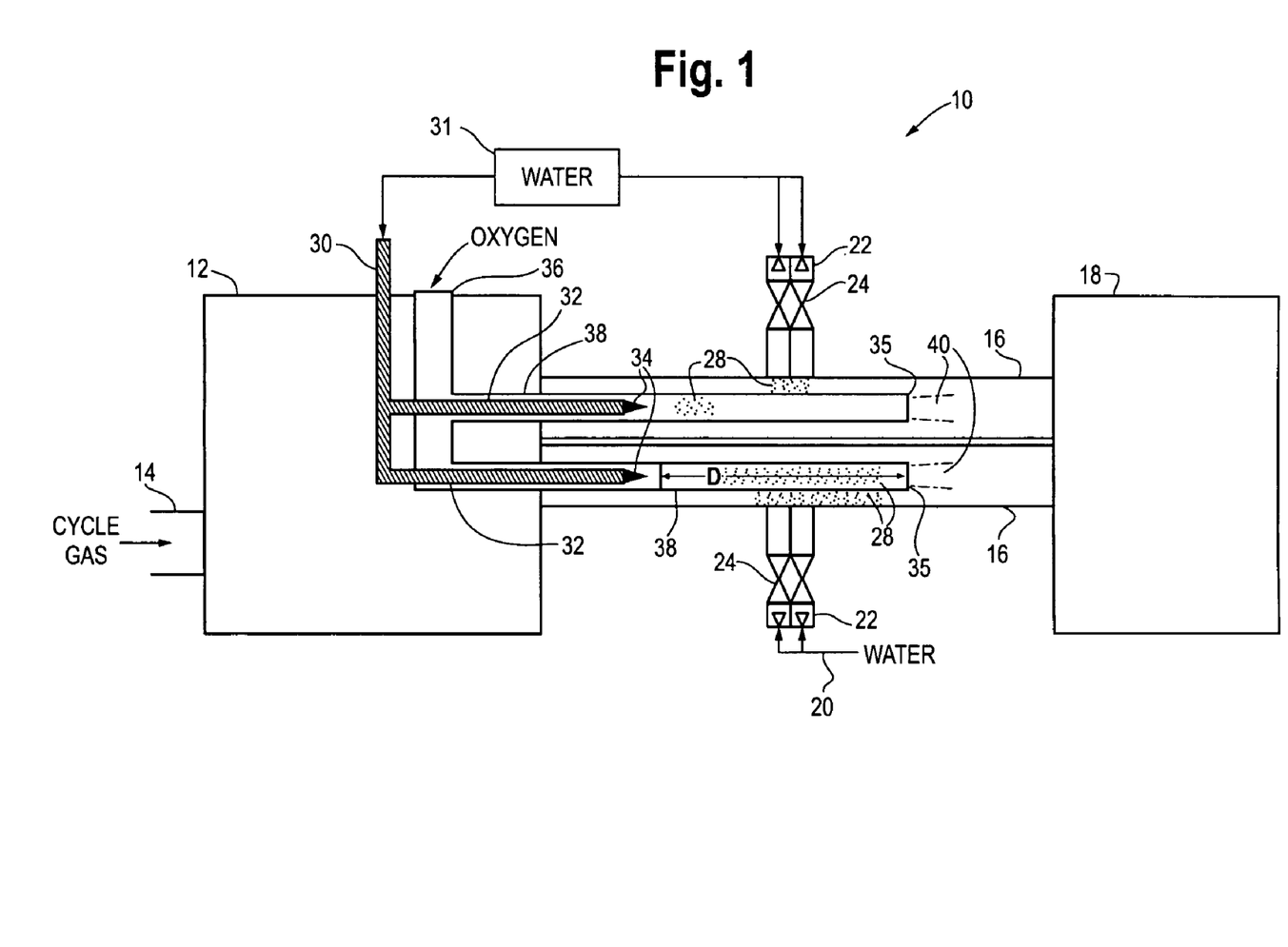
FIG. 1 is a schematic representation of a gas mixer for an industrial production system for catalytic gas-phase oxidation of a hydrocarbon-containing gas, showing a first embodiment of a means for introducing a coarse water droplet into the gas mixer in the form of (1) atomizers (nozzles) which inject coarse water droplets into one or more pipes carrying a hydrocarbon-containing gas stream and forming a mixing chamber for the two gases and (2) water pipes with coarse droplet-producing nozzles at the ends thereof concentrically located within oxygen pipes supplying oxygen to the mixing chamber.

FIG. 1 is a schematic representation of a gas mixer featuring a coarse water droplet environment where the hydrocarbon and oxygen gases meet. The gas mixer 10 includes a hydrocarbon-containing gas manifold 12 receiving recycled gas containing hydrocarbons such as ethylene from a source along an inlet pipe 14. One or more pipes 16 are connected to the hydrocarbon-containing gas manifold 12. Gas mixing occurs in the pipes 16, therefore the pipes 16 function as a mixing chamber for the gas mixer 10. Mixed gases are collected in a second manifold 18.

Figure 3:
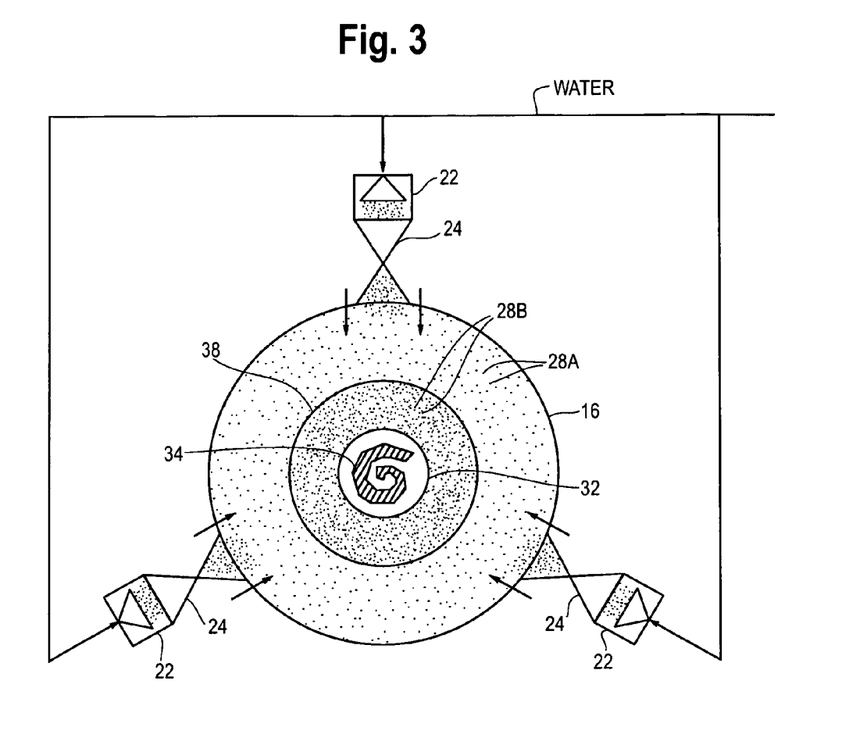
FIG. 3 is an alternative embodiment showing a different arrangement of nozzles spaced around the circumference of the pipe carrying the hydrocarbon-containing gas.

The gas mixer 10 features a means for producing a coarse water droplet environment in the pipes 16. In particular, water supply lines 20 are provided which supply water to atomizers (nozzles) 22. The atomizers 22 are of a design to produce coarse water droplets having a SMD of at least 200 microns. Valves 24 are placed downstream of the atomizers 22. Two or more atomizers 22 may be provided per pipe 16 and may be placed around the periphery of the pipe 16 as shown in FIG. 3. An alternative is to mount the spray nozzles 22 in the wall of the pipe 16 eliminating the valves 24. The arrangement of the nozzles can take many forms, with the water droplet sprays being coaxial with the cycle gas flow or at some angle with respect to this flow. In any event, a coarse water droplet environment is produced in the hydrocarbon-containing gas pipes 16.

Oxygen is supplied to the gas mixer via an oxygen gas manifold 36. Oxygen pipes 38, sometimes referred to in the art as "fingers", are connected to the manifold 36. The oxygen pipes 38 are coaxially located within the hydrocarbon pipes 16. Oxygen flows into the pipes 38 from the manifold 36 and flows out the distal end 35 of the pipes 38.

The mixer 10 further includes a water manifold 30 connected to a water source 31 which supplies water to pipes 32.

Each of the hydrocarbon pipes 16 has one or more oxygen pipes 38 placed within it, and each oxygen pipe 38 has a water pipe 32 coaxially within it, as shown in FIG. 1. A nozzle 34 is placed at the end of the water pipes 32. The nozzle 34, which may be of a variety of configurations, produces a cone or spray of coarse water droplets. The nozzles 34 are also designed to produce water droplets 28 having a size greater than 200 microns. The tip of the nozzle 34 is positioned a substantially distance "D" from the end 35 of the oxygen pipe 38. This distance D will vary depending on the application but may for example be between 1-5 meters for many applications. The distance D can be expressed in terms of multiples of the diameter of the oxygen pipe 38, such as between 5 and 500 times the diameter of the oxygen pipe 38. This design thereby ensures that entrained particles in the oxygen gas stream are wetted prior to entering the mixing zone 40.

Note that the spray of water drops (indicated at 28) created by the atomizers 22 is injected into the hydrocarbon-containing gas stream upstream of the mixing point 40. In particular, the position of the nozzles 22 is such that the it is also located a substantial distance "upstream" of the open ends 35 of the oxygen pipe 38 to thereby ensure that entrained particles in the hydrocarbon stream are wetted prior to entering the mixing zone 40. The coarse water drops created in the pipe 16 by both the nozzles 34 and 22 create what could be considered to be a "driving rainstorm" environment in the pipe 16 at the mixing zone 40.

Figure 4:
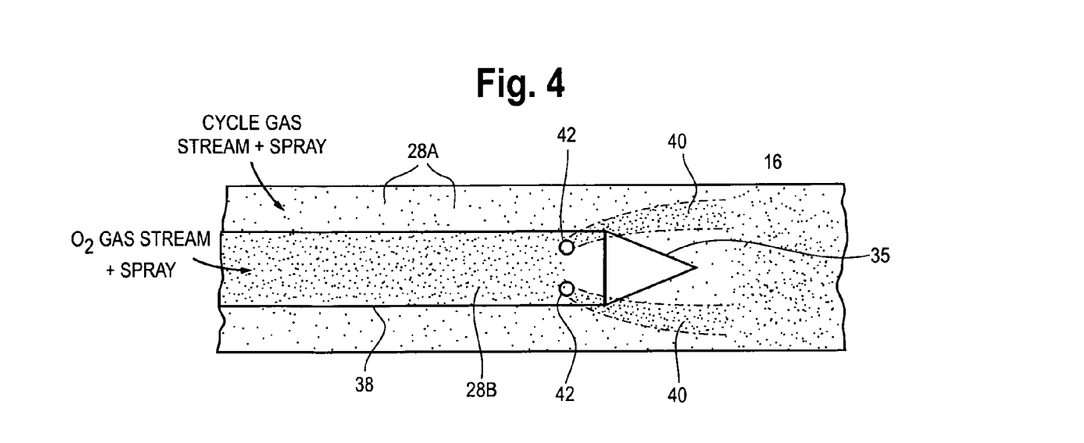
FIG. 4 is a more detailed illustration of the hydrocarbon and oxygen gas streams in the embodiment of FIGS. 1-3, showing the coarse water droplets created in both gas streams.

FIG. 4 is a more detailed illustration of the hydrocarbon and oxygen gas streams in a configuration where the oxygen pipe 38 has a closed end and the oxygen gas flows out through radial holes 42 formed in the walls of the pipe 38. FIG. 4 shows the coarse water droplets 28A and 28B created in both gas streams. The oxygen pipe 38 has transverse holes 42 through which the oxygen gas and water droplets 28B flows out of the pipe. The mixing zone where the oxygen gas/water droplet stream mixes with the hydrocarbon-containing gas stream and water droplets 28A is indicated at 40. The end 35 of the oxygen pipe 38 is closed and in the form of a cone in this embodiment with the holes 42 providing for egress of oxygen gas and water droplets.

The pipes 16 and the manifold 18 may have a drain (not shown) for collecting accumulated water and conducting the water from the pipes 16 and the manifold 18. Additionally, downstream there may be a device for removing water injected into the mixed gas stream.

In operation, hydrocarbon-containing gas enters manifold 12 where it is divided into one or more independent pipes 16. An oxygen-containing stream, preferably pure oxygen, enters manifold 36 where the stream is divided into one or more pipes 38, smaller than and concentric with pipes 16. Concentric pipes 38 extend some distance down the outer pipe 16 as determined by engineering calculations to be optimal for mixing and separation of the mixing zone 40 where the oxygen-containing gas mixes with the hydrocarbon-rich gas. In addition, a water stream enters manifold 30. The manifold is connected to the proximal ends of one or more pipes 32. The water pipes 32 are smaller in diameter and concentrically located within the oxygen pipe 38, which are concentric in pipes 16. Each oxygen pipe 38 has one water pipe 32 located within it. At the end of pipes 32 are affixed atomizing nozzles 34 designed for producing a spray of coarse water droplets having a droplet size of at least 200 microns SMD. The nozzle 34 at the end of pipe 32 terminates a substantial distance from the end of pipe 38 so as to cause the oxygen-containing gas to pass through a coarse water droplet environment before it mixes with the hydrocarbon-rich gas in the pipe 16.

As noted above, in addition to the coarse water droplet injected into the oxygen stream, water is introduced into the pipe 16 through one or more atomizing nozzles 22 such that a coarse water droplet environment is present in hydrocarbon-containing gas stream in the pipe 16 at the mixing point 40. Particles traveling with either the hydrocarbon-containing gas stream or the oxygen gas stream are wetted by the coarse water droplets, reducing the impact energy of the particle if it were to strike a surface of either pipe 16 or pipe 38. The water droplets also enhance heat transfer away from the particle and quench an ignition, if one should occur. The oxygen/hydrocarbon-containing gas mixture is re-gathered in manifold 18 for transfer to an optional downstream water removal processing station for removal of liquid water vapor from the collected gases, prior to entering a reactor located further downstream.

Figure 2:
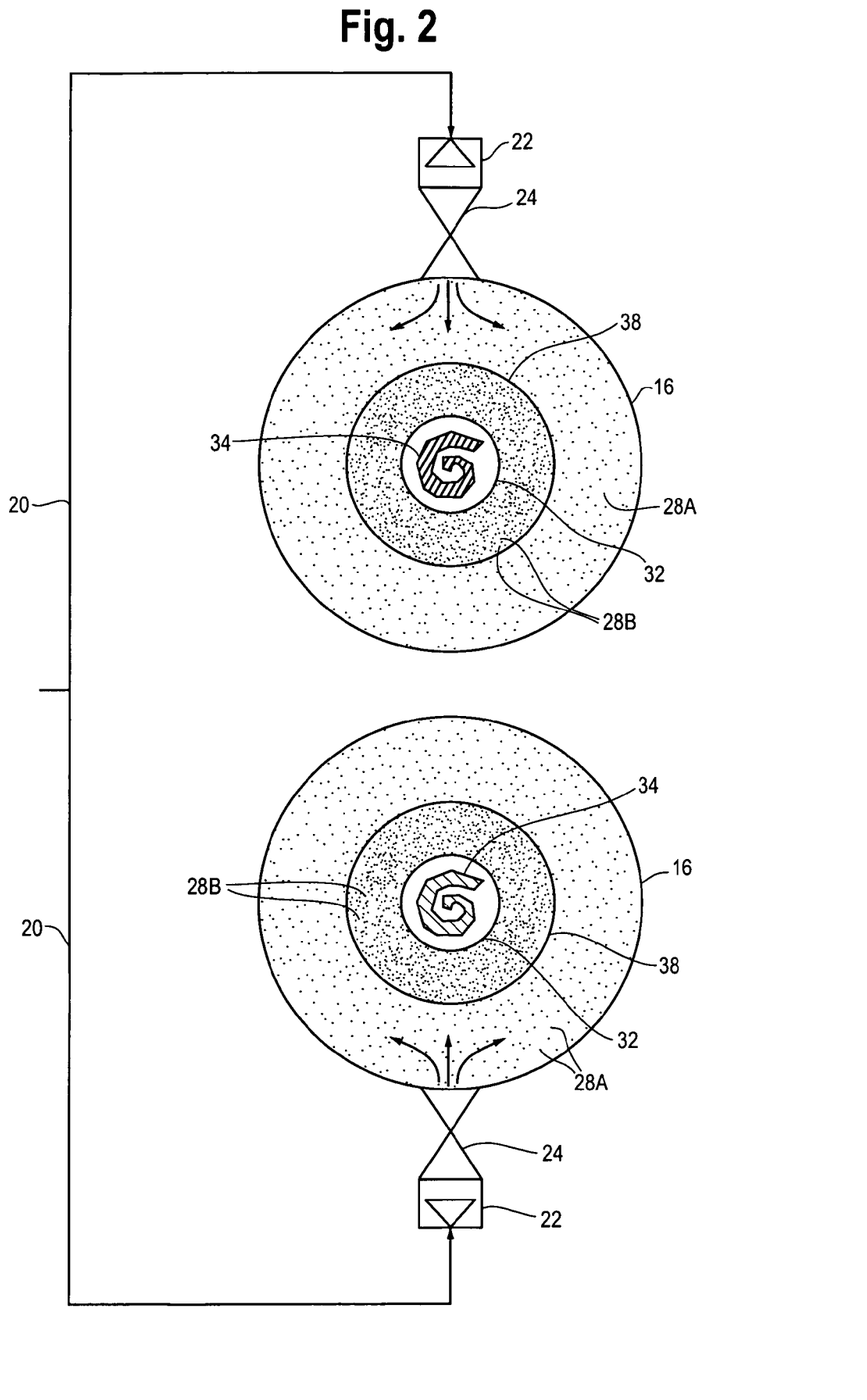
FIG. 2 is an end view of the hydrocarbon pipes of FIG. 1 showing the nozzles injecting water into the hydrocarbon pipes and the nozzles placed within the oxygen pipes.

FIG. 2 is an end view of two of the pipes 16 carrying the hydrocarbon-containing gas shown in FIG. 1 with coarse water droplets indicated at droplets 28A present in the hydrocarbon-containing gas stream due to atomizers 22 and also droplets 28B present in the oxygen gas stream due to nozzles 34.

While in FIG. 2 there is one oxygen pipe 38 per hydrocarbon pipe 16, this may of course vary, e.g., depending on the size and number of hydrocarbon pipes 16 in the gas mixer. For example, there may be 2, 3 or more oxygen pipes per hydrocarbon pipe 16, each containing a water pipe and nozzle.

FIG. 3 is an illustration of an alternative configuration of the nozzles 22 which inject a spray of water droplets into the hydrocarbon-containing gas pipe 16. In FIG. 3, the nozzles 22 are distributed around the periphery of the pipe 16. While three nozzles 22 are shown, the number may vary depending on the size of the pipe 16 and the velocity and distribution of the coarse water droplets produced by the atomizing nozzles 22. Furthermore, nozzles could be spaced along the length of the pipe 16.

The optional downstream water removal processing station may use a pressure vessel column to coalesce water vapor out of the mixed oxygen/hydrocarbon-containing gas stream. The recovered water may be processed by a carbonate scrubber to removed dissolved $CO_2$ from the recovered water and a water wash column to remove particulate matter, salts, and other impurities from the recovered water and recycle the water back into the water supplies of FIG. 1.

Suitable nozzles for use as the atomizers 22 and the nozzles 34 are available from suppliers such as BETE Fog Nozzle Inc., Greenfield Mass., or Spraying Systems Co., Wheaton Ill. A variety of types of devices can use used for creating the coarse water droplets, including single fluid spray nozzles, dual-fluid spray nozzles, ultrasonic devices for creating a spray of drops, or other means known in the art. The preferred nozzles produce water droplets having a size between 200 microns and 3000 microns SMD.

Example 2

Figure 5:
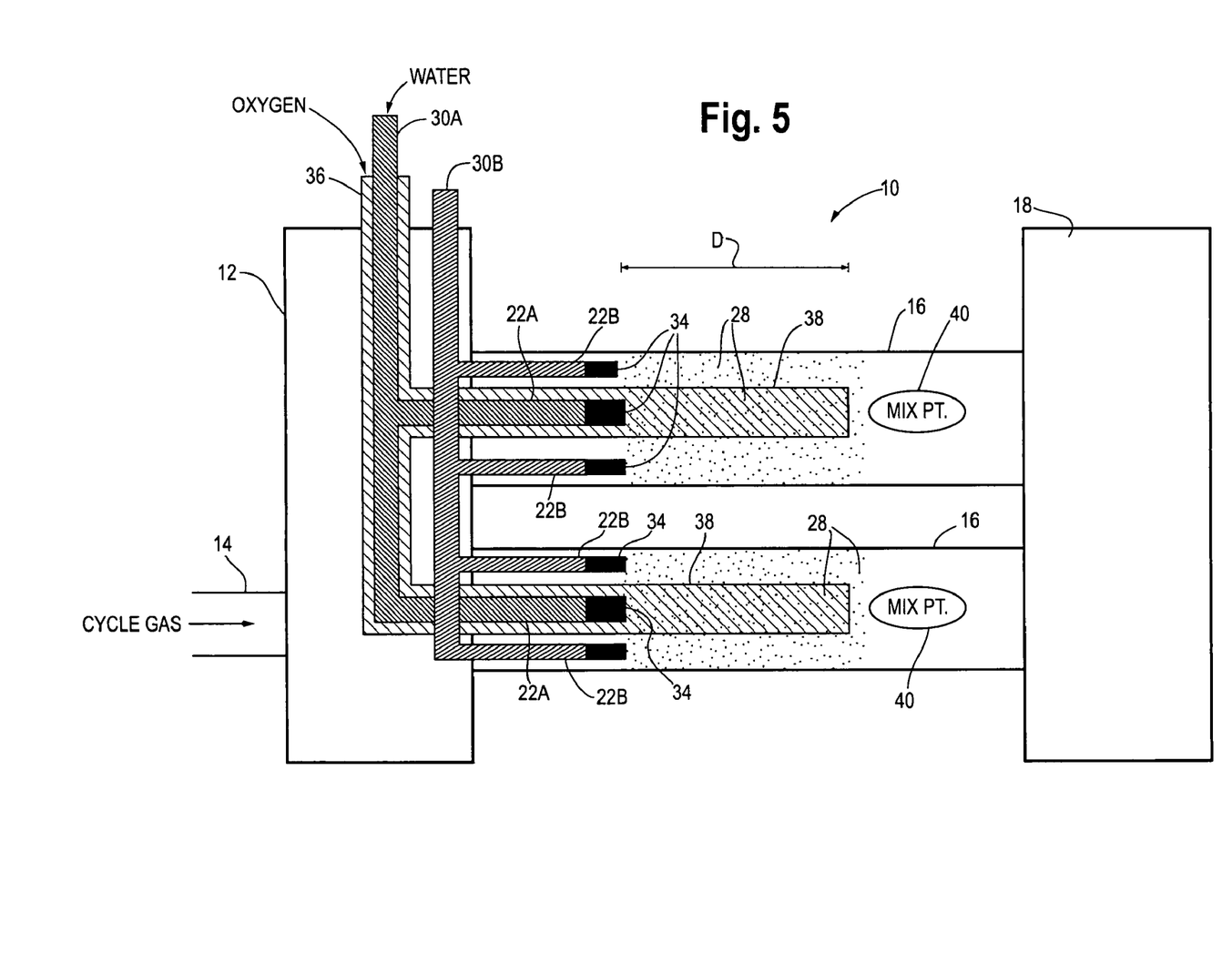
FIG. 5 is an illustration of an alternative configuration of the gas mixer of FIG. 1.

FIG. 5 is an illustration of a gas mixer 10 having a coarse water droplet environment. The construction and arrangement of the embodiment of FIG. 5 differs from FIG. 1 in several respects, including nozzles producing water drops in a coaxial direction in the hydrocarbon pipes 16, and a water manifold 30A which is located within the oxygen gas manifold 36.

In particular, the gas mixer 10 includes a first water manifold 30A connected to a source of water which is located within the oxygen manifold 36. Water pipes 22A are connected to the water manifold 30A and have a spray nozzle 34 placed at the end thereof. The water pipes 22A are positioned within the oxygen pipes 38. A second water manifold 30B is connected to a source of water. A second set of water pipes 22B are connected to the manifold 30B and placed within the hydrocarbon pipe 16 adjacent to the oxygen pipes 38. Coarse water drops 28 are injected into the hydrocarbon-containing gas stream by means of nozzles 34 positioned at the end of the water pipes 22B. Coarse water drops 28 are injected into the oxygen gas stream by means of nozzles 34 positioned at the ends of the water pipes 22A. The water drops serve to wet entrained particles in either the hydrocarbon or oxygen-containing gas streams. Thus, mixing of the oxygen-containing gas stream with the hydrocarbon-containing gas stream occurs downstream of the ends of the oxygen pipes 38 in a coarse water drop environment due to the spray of drops produced by the nozzles 34 in the pipe 16 and the nozzles in the water pipes positioned within the oxygen pipe 38.

The gas to liquid mass ratio for the gas mixers of this disclosure is in the range of 0.005 to 1 to 3 to 1.

In both Example 1 and Example 2, the water drops are preferably injected into hydrocarbon-containing gas stream and into the oxygen gas stream upstream of the mixing point where the oxygen and hydrocarbon-containing gases meet a distance "D" which is between 5 and 500 times the diameter of the oxygen pipes 38.

The term "coarse water droplet" is intended to encompass water droplets having a size having a size greater than 200 microns SMD, e.g., droplets between 200 microns and 3000 microns SMD.

In one embodiment, the temperature of the water used to produce the coarse water droplets is at ambient temperature. In an alternative embodiment, the water temperature is heated above ambient. For example, the water is heated to the temperature of the hydrocarbon-containing gas stream. In an EO production scenario, the temperature of the hydrocarbon recycle gas stream is typically between about 35-40 degrees C. and 65-70 degrees C. The water that is supplied to the spray nozzles can be either at ambient temperature, or water which has been heated to a temperature of between 35 and 70 degrees C.

While presently preferred embodiments have been described with particularity, variation from the specifics of the disclosed embodiments may be made without departure from the scope of the invention. All questions concerning scope of the invention are to be determined by reference to the appended claims.

We claim:

1. In an industrial production system for gas-phase partial oxidation of a hydrocarbon-containing gas, a method for mixing the hydrocarbon-containing gas with an oxygen containing gas, comprising the steps of:
    providing a gas mixer for mixing the oxygen containing gas with the hydrocarbon-containing gas;
    creating a coarse water droplet environment in the gas mixer;
    mixing the oxygen containing gas and the hydrocarbon-containing gas in the presence of the coarse water droplet environment.

2. The method of claim 1, wherein the gas mixer includes a pipe carrying a hydrocarbon-containing gas stream and at least one oxygen pipe located within the pipe carrying the hydrocarbon-containing gas stream, and wherein the introducing step comprises the step of injecting coarse water droplets into the pipe carrying the hydrocarbon-containing gas stream.

3. The method of claim 1, wherein the coarse water droplets are produced by nozzles designed to create water droplets having a size greater than 200 microns SMD.

4. The method of claim 1, wherein the coarse water droplets are further introduced into the gas mixer by means of a water pipe having a proximal end connected to a source of water and peripheral end having a spray nozzle, the water pipe positioned within the oxygen pipe, and wherein the nozzle creates a spray of droplets within the oxygen pipe.

5. The method of claim 4, wherein the oxygen pipe has a distal end through which oxygen gas flows out of the oxygen pipe and is mixed with the hydrocarbon-containing gas, and wherein the spray of droplets is created within the oxygen pipe a substantial distance from the distal end of the oxygen pipe.

6. The method of claim 1, wherein the hydrocarbon-containing gas comprises an ethylene containing gas.

7. The method of claim 5, wherein the oxygen pipe has a distal closed end and one or more holes for egress of oxygen gas and water droplets from the oxygen pipe.

8. The method of claim 5, wherein the distal closed end comprises a cone and wherein the holes are form in the pipe proximal to the cone.

9. In a gas mixer for an industrial production system for gas-phase partial oxidation of a hydrocarbon-containing gas, the improvement comprising:
    providing a means for creating a coarse water droplet environment in the gas mixer wherein an oxygen containing gas and the hydrocarbon-containing gas are mixed in the gas mixer in the presence of the coarse water droplet environment.

10. The improvement of claim 9, wherein the gas mixer further comprises a pipe carrying a hydrocarbon-containing gas stream forming a mixing chamber for the gas mixer, and wherein the means comprises a nozzle producing and injecting a stream of coarse water droplets into the mixing chamber.

11. The improvement of claim 9, wherein the means comprises a plurality of nozzles injecting a stream of coarse water droplets into the mixing chamber.

12. The improvement of claim 9, wherein the gas mixer further comprises a pipe carrying a hydrocarbon-containing gas stream forming a mixing chamber for the gas mixer, wherein an oxygen containing gas is supplied to a mixing chamber via an oxygen pipe, and wherein the means for creating the coarse water droplet environment further comprises a water pipe having a nozzle at the end thereof positioned within the oxygen pipe.

13. The improvement of claim 12, wherein the oxygen pipe has a distal closed end and one or more holes for egress of oxygen gas and water droplets from the oxygen pipe.

14. The improvement of claim 13, wherein the distal closed end comprises a cone and wherein the holes are form in the pipe proximal to the cone.

15. The improvement of claim 9, wherein the gas mixer further comprises:
    a hydrocarbon-containing gas manifold,
    a plurality of pipes coupled to the hydrocarbon-containing gas manifold carrying a hydrocarbon-containing gas stream, each forming a mixing chamber for the gas mixer,
    at least one oxygen gas pipe placed within each of the plurality of pipes, the oxygen pipes supplying a stream of oxygen containing gas to the pipes, and
    wherein the means for creating the coarse water droplet environment comprises a water pipe having a nozzle at the end thereof positioned each of the oxygen pipes.

16. The improvement of claim 15, wherein the means for creating the coarse water droplet environment further comprises at least one nozzle coupled to each of the plurality of pipes carrying the hydrocarbon-containing gas stream injecting a stream of coarse water droplets into the pipes carrying the hydrocarbon-containing gas stream.

17. A gas mixer for an industrial production system for gas-phase partial oxidation of a hydrocarbon-containing gas, comprising:

a hydrocarbon-containing gas manifold;

a pipe coupled to the hydrocarbon-containing gas manifold carrying a hydrocarbon-containing gas stream, the pipe forming a mixing chamber for the gas mixer;

an oxygen gas pipe placed within the pipe carrying the hydrocarbon-containing gas, the oxygen pipe supplying a stream of oxygen containing gas to the mixing chamber;

a water pipe coupled to a source of water and having a first nozzle at the end thereof positioned within the oxygen pipe, the nozzle producing a spray of coarse water droplets; and a second nozzle coupled to a source of water injecting coarse water droplets into the mixing chamber.

18. The gas mixer of claim 17, wherein the second nozzle injects coarse water droplets into the stream of hydrocarbon-containing gas at a point upstream of a mixing point where the hydrocarbon-containing gas is mixed with the oxygen containing gas.

19. The gas mixer of claim 17, wherein the spray of coarse water droplets produced by the nozzle within the oxygen pipe is created a substantial distance from a distal end of the oxygen pipe.

20. The method of claim 1, wherein the oxygen-containing gas is carried in an oxygen pipe which is placed within a pipe containing a hydrocarbon-containing gas and the two gases are mixed at a mixing point, and wherein the coarse water droplets are injected into the gas mixer at a point which is upstream of the mixing point a distance D, where D is between 5 and 500 times the diameter of the oxygen pipe.

* * * * *